United States Patent [19]
Floyd

[11] Patent Number: 5,932,785
[45] Date of Patent: Aug. 3, 1999

[54] SOYBEAN CULTIVAR CX284C

[75] Inventor: Thomas L. Floyd, Bloomington, Ill.

[73] Assignee: Dekalb Genetics Corporation, Dekalb, Ill.

[21] Appl. No.: 09/053,604

[22] Filed: Apr. 1, 1998

[51] Int. Cl.$^6$ .............................. A01H 5/00; A01H 5/10; A01H 1/02; C12N 5/04
[52] U.S. Cl. ..................... 800/312; 800/260; 435/415
[58] Field of Search ................. 800/200, 255, 800/DIG. 26, 312, 260, 300, 301, 302, 303; 435/415; 47/58, DIG. 1

[56] References Cited

U.S. PATENT DOCUMENTS

| | | | |
|---|---|---|---|
| 5,084,082 | 1/1992 | Sebastian | 71/90 |
| 5,304,728 | 4/1994 | Eby | 800/200 |
| 5,569,815 | 10/1996 | Eby | 800/200 |
| 5,576,474 | 11/1996 | Lussenden | 800/200 |

OTHER PUBLICATIONS

Allard, R.W., University of California, Davis, California. "Principles of Plant Breeding," Published by John Wiley & Sons, New York, University of California, Davis, California, pp. 50–98, 1960.

Bernard, ed., "Evaluation of Maturity Groups I and II of the U.S.D.A. Soybean Collection," pp. 1–3, 58–59, Sep. 1966.

Bernard, ed., "Evaluation of Maturity Groups III and IV of the U.S.D.A. Soybean Collection," pp. 1–3, 5a–5d, 8a–8d, 9a–9d, 14a–14d, 17a–17d, 24a–24d, and 25a–25d, Apr. 1969.

Fehr, "In: Soybeans: Improvement, Production and Uses," 2nd Edition, *Manograph* 16, p. 249 and 259, 1987.

Fehr, Walter R., Iowa State University. "Principles of Cultivar Development," vol. 1 Theory and Technique and vol. 2 Crop Species, Soybean, Published by Macmillian Publishing Company, New York, pp. 360–376, 1987.

GRIN Database Entry PI438065 (Aug. 9, 1994), From The Internet http://www.ars–grin.gov.

Nickell and Bernard, "Registration of L84–5873 and L84–5932 Soybean Germplasm Lines Resistant to Brown Stem Rot," *Crop Sci.*, 32:835, 1992.

Plant Variety Protection Certification Application 9000006.

Sneep, J. and A.J.T. Hendriksen, eds., "Plant Breeding Perspectives," Wageningen: Centre for Agricultural Publishing and Documentation, 1979.

Rieger et al. Glossary of Genetics: Classical and Molecular, Fifth Edition. Springer–Verlag, New York, pp. 192–193, 1991.

*Primary Examiner*—Elizabeth F. McElwain
*Attorney, Agent, or Firm*—Arnold, White & Durkee

[57] ABSTRACT

The instant invention relates to the novel soybean cultivar designated CX284c. Provided by the invention are the seeds, plants and derivatives of the soybean cultivar CX284c. Also provided by the invention are tissue cultures of the soybean cultivar CX284c and the plants regenerated therefrom. Still further provided by the invention are methods for producing soybean plants by crossing the soybean cultivar CX284c with itself or another soybean variety, as well as the plants produced by such methods.

21 Claims, No Drawings

SOYBEAN CULTIVAR CX284C

BACKGROUND OF THE INVENTION

1. Field of the Invention

The present invention relates generally to the field of soybean breeding. In particular, the invention relates to the novel soybean cultivar CX284c.

2. Description of Related Art

There are numerous steps in the development of any novel, desirable plant germplasm. Plant breeding begins with the analysis and definition of problems and weaknesses of the current gerrnplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable cultivar. This approach has been used extensively for breeding disease-resistant cultivars (Bowers et al., 1992; Nickell and Bernard, 1992). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial cultivars. Those still deficient in a few traits may be used as parents to produce new populations for further selection.

These processes, which lead to the final step of marketing and distribution, may take as much as eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard cultivars. Single observations are generally inconclusive, while replicated observations provide a better estimate of genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line de novo, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of progeny from the superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines as well as the phenotype of the hybrid influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population (or later depending upon the breeders objectives); then, beginning in the $F_3$, the best individuals in the best families can be selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar which is the recurrent parent. The source of the trait to be transferred is called the donor or nonreccurent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987a,b).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are to maximize the amount of grain produced on the land used and to supply food for both animals and humans. To accomplish this goal, the soybean breeder must select and develop soybean plants that have the traits that result in superior cultivars.

SUMMARY OF THE INVENTION

One aspect of the present invention relates to soybean seed designated CX284c. The invention also relates to plants produced by growing the seed of the soybean cultivar designated CX284c, as well as the derivatives of such plants. As used herein, the term "plant" includes plant cells, plant protoplasts, plant cells of a tissue culture from which soybean plants can be regenerated, plant calli, plant clumps, and plant cells that are intact in plants or parts of plants, such as pollen, flowers, seeds, pods, leaves, stems, and the like.

Another aspect of the invention relates to a tissue culture of regenerable cells of the soybean cultivar CX284c, as well as plants regenerated therefrom, wherein the regenerated soybean plant is capable of expressing all the physiological and morphological characteristics of a plant grown from the soybean seed designated CX284c.

Yet another aspect of the current invention is a soybean plant comprising a gene conversion of the soybean cultivar CX284c, wherein the soybean plant is otherwise capable of expressing all the physiological and morphological characteristics of the soybean cultivar CX284c. In particular embodiments of the invention, the gene conversion may comprise a transgenic gene. In still other embodiments of the invention, the gene conversion may comprise a dominant or recessive allele. The gene conversion may confer potentially any trait upon the converted plant, including herbicide resistance, insect resistance, resistance to bacterial, fungal, or viral disease, male fertility or sterility, and improved nutritional quality.

Still yet another aspect of the invention relates to a first generation ($F_1$) hybrid soybean seed produced by crossing a plant of the soybean cultivar CX284c to a second soybean plant. Also included in the invention are the $F_1$ hybrid soybean plants grown from the hybrid seed produced by crossing the soybean cultivar CX284c to a second soybean plant. Still further included in the invention are the seeds of an $F_1$ hybrid plant produced with the soybean cultivar CX284c as one parent, the second generation ($F_2$) hybrid soybean plant grown from the seed of the $F_1$ hybrid plant, and the seeds of the $F_2$ hybrid plant.

Still yet another aspect of the invention is a method of producing soybean seeds comprising crossing a plant of the soybean cultivar CX284c to any second soybean plant, including another CX284c plant. In particular embodiments of the invention, the method comprises the steps of a) planting seeds of the soybean cultivar CX284c; b) cultivating soybean plants resulting from said seeds until said plants bear flowers; c) allowing fertilization of the flowers of said plants; and, d) harvesting seeds produced from said plants.

Still yet another aspect of the invention is a method of producing hybrid soybean seeds. In particular embodiments of the invention, the method comprises the steps of a) planting in pollinating proximity seeds of soybean cultivar CX284c and a second, nonisogenic soybean cultivar, b) cultivating the soybean plants grown from said seeds until said plants bear flowers; c) emasculating the male flowers of either the plants grown from the seeds of the soybean cultivar CX284c or the second soybean cultivar; d) allowing cross pollination to occur between said soybean cultivars; and e) harvesting seeds produced on said emasculated plants.

DETAILED DESCRIPTION OF THE INVENTION

The instant invention provides the plants, seeds and derivatives of the soybean cultivar CX284c, as well as methods for making the same. Also provided by the current invention are single and multiple gene conversions of the soybean cultivar CX284c. The terms single gene or multiple gene converted plant, as used herein, refer to those soybean plants which are developed by the plant breeding technique of backcrossing. Through backcrossing, essentially all of the desired morphological and physiological characteristics of a variety may be recovered in addition to the gene or genes transferred into the variety via the backcrossing technique. Backcrossing methods can be used with the present invention to improve or introduce one or more characteristics into the current soybean variety.

The term backcrossing, as used herein, refers to the repeated crossing of a hybrid progeny back to one of the parental soybean plants for that variety. The parental soybean plant which contributes the gene(s) for the desired characteristic(s) is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent, as it is used for several rounds in the backcrossing protocol (Poehlman & Sleper, 1994; Fehr, 1987a,b). In a typical backcross protocol, the original variety of interest (recurrent parent) is crossed to a second variety (nonrecurrent parent) that carries the gene (s) of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the transferred gene(s) from the nonrecurrent parent. The process may be carried out as many times as desired, using either the same or another nonrecurrent parent, to introduce multiple traits into CX284c, yet retain all of the desirable agronomic properties of the starting line.

The selection of a suitable recurrent parent is an important step for a successful backcrossing procedure. The goal of a backcross protocol is to alter or substitute a particular trait or characteristic in the original cultivar. To accomplish this, one or more traits of the recurrent variety is modified or substituted with the desired gene from the nonrecurrent parent. Thereby, while retaining essentially all of the desired genetic background of the recurrent parent, and therefore the desired agronomic characteristics, one or more desirable traits from the nonrecurrent parent(s) are added. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristics has been successfully transferred.

Many single gene traits have been identified that are not regularly selected for in the development of a new cultivar but that can be improved by backcrossing techniques. Single gene traits may or may not be transgenic. Examples of these traits are well known to those of skill in the art of soybean breeding and include, for example, genes conferring bacterial, fungal, or viral disease resistance, insect resistance, male fertility or sterility, enhanced nutritional quality, and yield enhancement. These genes are generally inherited through the nucleus.

One type of single gene trait having particular utility is a gene which confers herbicide resistance, particularly resistance to the herbicide glyphosate. Glyphosate inhibits the action of the enzyme EPSPS, which is active in the biosynthetic pathway of aromatic amino acids. Inhibition of this enzyme leads to starvation for the amino acids phenylalanine, tyrosine, and tryptophan and secondary metabolites derived therefrom. Mutants of this enzyme are available which are resistant to glyphosate. For example, U.S. Pat. No. 4,535,060 describes the isolation of EPSPS mutations which confer glyphosate resistance upon organisms having the *Salmonella typhimurium* gene for EPSPS, aroA. A mutant EPSPS gene having similar mutations has also been cloned from *Zea mays*. The mutant gene encodes a protein with amino acid changes at residues 102 and 106. When these or other similar genes are introduced into a plant by genetic transformation, a herbicide resistant phenotype results.

Plants having inherited a transgene comprising a mutated EPSPS gene may, therefore, be directly treated with the herbicide glyphosate without the result of significant damage to the plant. This phenotype provides farmers with the benefit of controlling weed growth in a field of plants having the herbicide resistance trait by application of the broad spectrum herbicide glyphosate. For example, one could apply the herbicide ROUNDUP™, a commercial formulation of glyphosate manufactured and sold by the Monsanto Company, over the top in fields where the glyphosate resistant soybeans are grown. The herbicide application rates may range from 4 ounces of ROUNDUP™ to 256 ounces ROUNDUP™ per acre. More preferably, about 16 ounces to about 64 ounces per acre of ROUNDUP™ may be applied to the field. However, the application rate may be increased or decreased as needed, based on the abundance and/or type of weeds being treated. Additionally, depending on the location of the field and weather conditions, which will influence weed growth and the type of weed infestation, it may be desirable to conduct further glyphosate treatments. The second glyphosate application will also typically comprise an application of about 16 ounces to about 64 ounces of ROUNDUP™ per acre treated. Again, the treatment rate may be adjusted based on field conditions. Such methods of application of herbicides to agricultural crops are well known in the art and are summarized in general in Anderson, 1983.

It will be understood to those of skill in the art that a herbicide resistance gene, such as a mutant EPSPS glyphosate resistance transgene, may be used for direct selection of plants having the resistance gene. For example, by applying about 16 to 64 ounces of ROUNDUP™ per acre to a collection of soybean plants which either have or lack the herbicide resistance trait, the plants lacking the trait will be killed or damaged. In this way, the herbicide resistant plants may be selected and used for commercial applications or advanced in certain breeding protocols. This application may find particular use during the breeding and development of herbicide resistant elite soybean cultivars.

Flower color is an example of a recessive trait. In this example, the progeny resulting from the first backcross generation ($BC_1$) are grown and selfed. The selfed progeny from the $BC_1$ plant are grown to determine which $BC_1$ plants carry the recessive gene for flower color. In other recessive traits, additional progeny testing, for example growing additional generations such as the $BC_1F_2$, may be required to determine which plants carry the recessive gene.

Selection of soybean plants for breeding is not necessarily dependent on the phenotype of a plant and instead can be based on genetic investigations. For example, one may find a suitable genetic marker, such as a restriction fragment length polymorphism, which is closely genetically linked to a trait of interest. This marker may therefore be used to identify the presence or absence of a trait in the offspring of a particular cross, and hence may be used in selection of progeny for continued breeding. This technique may commonly be referred to as marker assisted selection. Any other type of genetic or other assay which is able to identify the relative presence or absence of a trait of interest in a plant may be also be useful for breeding purposes. Exemplary procedures for marker assisted selection and breeding of soybeans are disclosed in U.S. Pat. No. 5,437,697, and U.S. Pat. No. 5,491,081, both of which disclosures are specifically incorporated herein by reference in their entirety. Such methods will be of particular utility in the case of recessive traits and variable phenotypes, or where conventional assays are expensive, time consuming or otherwise disadvantageous.

I. Definitions

In the description and tables which follow, a number of terms are used. In order to provide a clear and consistent understanding of the specification and claims, including the scope to be given such terms, the following definitions are provided:

A: When used in conjunction with the word "comprising" or other open language in the claims, the words "a" and "an" denote "one or more."

Allele: Any of one or more alternative forms of a gene, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more gene conversions from one genetic background into another.

Brown Stem Rot: This is a visual disease score from 1 to 9 comparing all genotypes in a given test. The score is based on leaf symptoms of yellowing and necrosis caused by brown stem rot. A score of 1 indicates no symptoms. Visual scores range to a score of 9 which indicates severe symptoms of leaf yellowing and necrosis.

Chromatography: A technique wherein a mixture of dissolved substances are bound to a solid support followed by passing a column of fluid across the solid support and varying the composition of the fluid. The components of the mixture are separated by selective elution.

Cross-pollination: Fertilization by the union of two gametes from different plants.

Crossing: The mating of two parent plants.

Diploid: A cell or organism having two sets of chromosomes.

Emasculate: The removal of plant male sex organs or the inactivation of the organs with a cytoplasmic or nuclear factor conferring male sterility.

Emergence: This is a score indicating the ability of a seed to emerge from the soil after planting. Each genotype is given a 1 to 9 score based on its percent of emergence. A score of 1 indicates an excellent rate and percent of emergence, an intermediate score of 5 indicates average ratings and a 9 score indicates a very poor rate and percent of emergence.

Enzymes: Molecules which can act as catalysts in biological reactions.

$F_1$ Hybrid: The first generation progeny of the cross of two nonisogenic plants.

Gene Converted (Conversion) Plant: Plants which are developed by a plant breeding technique called backcrossing, wherein essentially all of the desired morphological and physiological characteristics of a cultivar are recovered in addition to the gene(s) transferred into the cultivar via the backcrossing technique.

Genotype: The genetic constitution of a cell or organism.

Haploid: A cell or organism having one set of the two sets of chromosomes in a diploid.

Iron-Deficiency Chlorosis: A plant scoring system ranging from 1 to 9 based on visual observations. A score of 1 means no stunting of the plants or yellowing of the leaves and a score of 9 indicates the plants are dead or dying caused by iron-deficiency chlorosis, a score of 5 means plants have intermediate health with some leaf yellowing.

Linkage: A phenomenon wherein alleles on the same chromosome tend to segregate together more often than expected by chance if their transmission was independent.

Lodging Resistance: Lodging is rated on a scale of 1 to 9. A score of 1 indicates erect plants. A score of 5 indicates plants are leaning at a 45 degree(s) angle in relation to the ground and a score of 9 indicates plants are laying on the ground.

Marker: A readily detectable phenotype, preferably inherited in codominant fashion (both alleles at a locus in a diploid heterozygote are readily detectable), with no environmental variance component, i.e., heritability of 1.

Maturity Date: Plants are considered mature when 95% of the pods have reached their mature color. The maturity date is typically described in measured days from January first, which may be referred to as "Julian Days."

Phenotype: The detectable characteristics of a cell or organism, which characteristics are the manifestation of gene expression.

Phytophthora Tolerance: Tolerance to Phytophthora root rot is rated on a scale of 1 to 9, with a score of 1 being the best or highest tolerance ranging down to a score of 9, which indicates the plants have no tolerance to Phytophthora.

Plant Height: Plant height is taken from the top of soil to the top node of the plant and is measured in inches.

Regeneration: The development of a plant from tissue culture.

Seed Yield (Bushels/Acre): The yield in bushels/acre is the actual yield of the grain at harvest.

Self-pollination: The transfer of pollen from the anther to the stigma of the same plant.

Shattering: The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Tissue Culture: A composition comprising isolated cells of the same or a different type or a collection of such cells organized into parts of a plant. Exemplary procedures for preparing tissue cultures of regenerable soybean cells, and regenerating soybean plants therefrom, are disclosed in, for example, U.S. Pat. No. 4,992,375; U.S. Pat. No. 5,015,580; U.S. Pat. No. 024,944, and U.S. Pat. No. 5,416,011, each of which disclosure is specifically incorporated herein by reference in its entirety.

Transgene: A genetic sequence which has been introduced into the genome of a soybean plant by transformation.

II. Variety Description Information

Soybean cultivar CX284c has superior characteristics and is an $F_3$ plant selection from the cross of $CX340c^2 \times CX259$. The origin and breeding history of the CX284c cultivar are as follows:

| | |
|---|---|
| Winter 1990–91 | The cross of CX340c x CX259 was made. |
| Summer 1991 | The cross of CX340c(CX340c x CX259) was made. |
| Winter 1991–92 | $F_1$ generation was grown (range 1, row 43). |
| | $F_2$ generation was grown (range 43, rows 1–15). |
| Summer 1992 | $F_3$ generation was grown (range 610, rows 29–40 through range 611, rows 1–28). |
| Summer 1993 | $F_4$ generation was grown. Range 880, row 26 was selected. |
| Winter 1993–94 | $F_5$ generation was grown. |
| Summer 1994 | $F_6$ generation was grown. |
| Summer 1995 | $F_7$ generation was grown. |
| Summer 1996 | $F_8$ generation was grown. |
| Winter 1996–97 | $F_9$ generation was grown. |
| Summer 1997 | $F_{10}$ generation was grown. |
| Spring 1998 | $F_{11}$ generation was released as CX284c. |

The inventors believe that CX284c is most similar to soybean variety CX297 (PVP application no. 9600310), however, CX284c differs from this cultivar in at least the following traits: CX284c has white flowers, is resistant to Race 3 Soybean Cyst Nematode and has normal tolerance to sulfonylurea herbicide, whereas, CX297 has purple flowers, is susceptible to Race 3 Soybean Cyst nematode and has enhanced tolerance to sulfonylurea herbicides.

The results of an objective description of the variety, based on data collected at Bloomington, Ill. were as follows:
SEED SHAPE: Spherical
SEED COAT COLOR (Mature Seed): Yellow
SEED COAT LUSTER(Mature Hand Shelled Dull Seed):
SEED SIZE (Mature Seed): 17.5 g/100 seed
HILUM COLOR: (Mature Seed) Black
COTYLEDON COLOR (Mature Seed): Yellow
SEED PROTEIN PEROXIDASE ACTIVITY: High
SEED PROTEIN ELECTROPHORECTIC — BAND:
HYPOCOTYL COLOR: Green
LEAFLET SHAPE: Ovate
LEAFLET SIZE: Medium
LEAF COLOR: Medium Green
FLOWER COLOR: White
POD COLOR: Tan
PLANT PUBESCENCE COLOR: Tawny
PLANT TYPE: Medium
PLANT HABIT: Indeterminate
MATURITY GROUP: II

DISEASE REACTION: (0 = NOT TESTED; 1 = SUSCEPTIBLE; 2 = RESISTANT)

| BACTERIAL DISEASES | | FUNGAL DISEASES | |
|---|---|---|---|
| Bacterial Pustule: | 0 | Brown Spot: | 0 |
| Bacterial Blight: | 0 | Frogeye Leaf Spot: | 0 |
| Wildfire: | 0 | Target Spot: | 0 |
| | | Downy Mildew: | 0 |
| VIRAL DISEASES | | Powdery Mildew: | 0 |
| Bud Blight: | 0 | Brown Stem Rot: | Resistant* |
| Yellow Mosaic: | 0 | Stem Canker: | 0 |
| Cowpea Mosaic: | 0 | Pod and Stem Blight: | 0 |
| Pod Mottle: | 0 | Purple Seed Stain: | 0 |
| Seed Mottle: | 0 | Rhizoctonia Root Rot: | 0 |
| | | Sclerotinia White Mold: | Intermediate** |
| | | Sudden Death Syndrome: | Resistant*** |
| NEMATODE DISEASES | | Phytophthora Rot: | 1 |
| Soybean Cyst Nematode: | | Race(s): | |
| Race 1: | 2 | Race 1: | 0 |
| Race 3: | 2 | Race 2: | 0 |
| Lance Nematode: | 0 | Race 3: | 0 |
| Southern Root Knot Nematode: | 0 | Race 4: | 0 |
| | | Race 5–9: | 0 |
| Northern Root Knot Nematode: | 0 | | |
| Peanut Root Knot Nematode: | 0 | | |
| Reniform Nematode: | 0 | | |

PHYSIOLOGICAL RESPONSES: (0 = NOT TESTED; 1 = SUSCEPTIBLE; 2 = RESISTANT)

Iron Chlorosis on Calcareous Intermediate^
Soil:
Other: 0

INSECT REACTION: (0 = NOT TESTED; 1 = SUSCEPTIBLE; 2 = RESISTANT)

| | |
|---|---|
| Mexican Bean Beetle: | 0 |
| Potato Leaf Hopper: | 0 |
| Other: | 0 |

*DEKALB's score for brown stem rot is 2 (Rating scale 1–9: 1 = most resistant)
**DEKALB's score for Sclerotinia white mold is 5 (Rating scale 1–9: 1 = most resistant)
***DEKALB's score for sudden death syndrome is 2 (Rating scale 1–9: 1 = most resistant)
^DEKALB's score for iron chlorosis is 5 (Rating scale 1–9: 1 = most resistant)

Soybean variety CX284c has been judged to be uniform for breeding purposes and testing after four generations of selfing. CX284c was reproduced and judged uniform and stable for an additional seven generations. Variety CX284c shows no variants other than what would normally be expected due to environment or that would occur for almost any characteristic during the course of repeated sexual reproduction. Some of the criteria used to select in various generations include: seed yield, lodging resistance, emergence, seedling vigor, disease tolerance, maturity, plant height and shattering resistance.

III. Variety Comparison

Direct comparisons were made between CX284c and competing commercial varieties. Traits measured were yield, maturity, moisture, lodging, plant height, field emergence, and seedling vigor. The results of the variety comparison are presented below. The comparison indicates the number of tests in which the varieties were compared, the deviation or difference of the results, the test means, and the traits which showed a significant difference and the significance level.

| VARIETIES COMPARED | TYPE | SEL % M | YLD BU/A | MAT DAYS | MST % | LDG RAT | PLTHT IN | FDEMR RAT | VIG RAT |
|---|---|---|---|---|---|---|---|---|---|
| CX284c | R 100 | 101.6 | 52.0 | 268.6 | 10.8 | 2.8 | 36.8 | 2.7 | 2.8 |
| CX260c |  | 99.8 | 49.4 | 269.1 | 10.8 | 3.7 | 36.6 | 3.0 | 2.9 |
| Deviation |  | 1.8 | 2.6 | −0.5 | 0.0 | −0.9 | 0.2 | −0.3 | −0.2 |
| Test Mean |  | 100.0 | 48.4 | 267.0 | 10.6 | 4.0 | 34.8 | 3.8 | 3.5 |
| Sig |  | * | ** |  |  | ** |  | + |  |
| CX284c | R 79 | 101.6 | 52.2 | 269.2 | 10.7 | 2.7 | 36.8 | 2.6 | 2.7 |
| CX292c |  | 97.1 | 49.2 | 270.9 | 10.7 | 2.1 | 36.1 | 2.9 | 3.0 |
| Deviation |  | 4.5 | 3.0 | −1.7 | 0.0 | 0.7 | 0.7 | −0.3 | −0.3 |
| Test Mean |  | 100.0 | 48.5 | 267.7 | 10.5 | 3.9 | 34.9 | 3.7 | 3.5 |
| Sig |  | ** | ** | ** |  | ** |  | * | + |

Significance levels are indicated as: + = 10%, * = 5%, ** = 1%
TYPE = Research - No. of tests
SEL % M = Selection Index (percentage of test mean)
YLD BU/A = Yield (bushels/acre)
MAT DAYS = Maturity (days)
MST % = Moisture (percentage)
LDG RAT = Lodging Rating (scale: 1–9, 1 = best)
PLTHT IN = Plant Height (inches)
FDEMR RAT = Field Emergence Rating (scale: 1–9, 1 = best)
VIG RAT = Seedling Vigor Rating (scale: 1–9, 1 = best)

IV. Deposit Information

A deposit of the DEKALB Genetics propriety soybean cultivar CX284c, disclosed above and recited in the appended claims, has been made with the American Type Culture Collection (ATCC), 10801 University Blvd., Manassas, Va. 20110-2209. The date of deposit on Nov. 4, 1998. All restrictions upon the deposit have been removed, and the deposit is intended to meet all of the requirements of 37 C.F.R. §1.801–1.809. The accession number for those deposited seeds of soybean cultivar CX284c is ATCC Accession No. 203415. The deposit will be maintained in the depository for a period of 30 years, or 5 years after the last request, or for the effective life of the patent, whichever is longer, and will be replaced if necessary during that period.

REFERENCES

The following references, to the extent that they provide exemplary procedural or other details supplementary to those set forth herein, are specifically incorporated herein by reference.

U.S. Pat. No. 4,992,375
U.S. Pat. No. 5,015,580
U.S. Pat. No. 5,024,944
U.S. Pat. No. 5,416,011
U.S. Pat. No. 5,437,697
U.S. Pat. No. 5,491,081
Allard, R. W., University of California, Davis, Calif. "Principles of Plant Breeding," Published by John Wiley & Sons, New York, University of California, Davis, Calif., p. 50–98, 1960.
Anderson, W. P., Weed Science Principles, West Publishing Company, 1983.
Bowers, G. R., Paschall, E. H., Bernard, R. L.; and Goodman, R. M., "Inheritance of Resistance to Soybean Mosaic Virus in 'Buffalo' and HLS Soybean" Crop science. v. 32(1) p. 67–72, 1992.
Fehr, "In: Soybeans: Improvement, Production and Uses," 2nd Edition, *Manograph* 16, p.259, 1987a.
Fehr, W. R., "Principles of Cultivar Development," vol. 1 Theory and Technique and vol. 2 Crop Species, Soybean, Iowa State University, Published by Macmillian Publishing Company, New York, p. 360–376, 1987b.
Nickell, C. D., and Bernard, R. L., "Registration of L84-5873 and L84-5932 Soybean Germplasm Lines Resistant to Brown Stem Rot," Crop Science. v. 32(3) p. 835, 1992.
Poehlman, J., and Sleper, D. "Breeding Field Crops" Published by the Iowa State University Press, Ames, 1994.
Simmonds, N., "Principles of crop improvement" Published by, Longman, Inc., New York, p. 369–399, 1979.
Sneep, J., and Hendriksen, A., "Plant Breeding Perspectives," Wageningen: Center for Agricultural Publishing and Documentation, 1979.

What is claimed is:

1. Soybean seed designated CX284c, wherein a sample of said seed has been deposited under ATCC Accession No. 203415.

2. A plant produced by growing the seed of claim 1.

3. Pollen of the plant of claim 2.

4. An ovule of the plant of claim 2.

5. A cell of the soybean plant of claim 2.

6. A soybean plant having all of the physiological and morphological characteristics of the plant of claim 2.

7. A tissue culture of regenerable cells of the soybean cultivar CX284c, wherein a sample of the seed of said soybean cultivar CX284c has been deposited under ATCC Accession No. 203415.

8. A soybean plant regenerated from the tissue culture of claim 7, wherein the regenerated soybean plant is capable of expressing all the physiological and morphological characteristics of a plant grown from a soybean seed designated CX284c, and wherein a sample of said seed has been deposited under ATCC Accession No. 203415.

9. A soybean plant comprising a single gene conversion of the soybean cultivar CX284c, wherein said soybean plant is otherwise capable of expressing all the physiological and morphological characteristics of the soybean cultivar CX284c, and wherein a sample of the seed of said soybean cultivar CX284c has been deposited under ATCC Accession No. 203415.

10. The soybean plant of claim 9, wherein said single gene was stably inserted into a soybean genome by transformation.

11. The soybean plant of claim 9, wherein said gene conversion comprises a dominant allele.

12. The soybean plant of claim 9, wherein said gene conversion comprises a recessive allele.

13. The soybean plant of claim 9, wherein said gene conversion confers herbicide resistance.

14. The soybean plant of claim 9, wherein said gene conversion confers insect resistance.

15. The soybean plant of claim 9, wherein said gene conversion confers resistance to bacterial, fungal, or viral disease.

16. The soybean plant of claim 9, wherein said gene conversion confers male sterility.

17. A first generation ($F_1$) hybrid soybean seed produced by crossing a plant of the soybean cultivar CX284c to a second distinct soybean plant, wherein a sample of the seed of said soybean cultivar CX284c has been deposited under ATCC Accession No. 203415.

18. A first generation ($F_1$) hybrid soybean plant produced by growing the seed of claim 17.

19. Seed of the first generation $F_1$ hybrid soybean plant of claim 18.

20. A method of producing soybean seed comprising:
   a) planting seed of the soybean cultivar CX284c, wherein a sample of said seed has been deposited under ATCC Accession No. 203415;
   b) growing soybean plants from said seed until said plants bear flowers;
   c) allowing said flowers to be pollinated; and,
   d) harvesting seed produced from said plants.

21. A method of producing hybrid soybean seed comprising the steps of:
   a) planting seed of soybean cultivar CX284c and a second distinct soybean cultivar, wherein a sample of the seed of said soybean cultivar CX284c has been deposited under ATCC Accession No. 203415;
   b) growing soybean plants from said seed until said plants bear flowers;
   c) emasculating a flower of either soybean cultivar;
   d) cross pollinating said flower; and
   e) harvesting seed resulting from said cross pollinating.

* * * * *